(12) United States Patent
Mertin et al.

(10) Patent No.: US 8,545,829 B2
(45) Date of Patent: Oct. 1, 2013

(54) PHARMACEUTICAL PREPARATIONS FOR ORAL ADMINISTRATION, CONTAINING ION-EXCHANGE RESINS LOADED WITH ACTIVE INGREDIENTS AND INTRINSICALLY VISCOUS GELLING AGENTS AS THICKENING AGENTS

(75) Inventors: Dirk Mertin, Langenfeld (DE); Markus Edingloh, Leverkusen (DE); Gert Daube, Engelskirchen (DE)

(73) Assignee: Bayer Intellectual Property GmbH (DE)

( * ) Notice: Subject to any disclaimer, the term of this patent is extended or adjusted under 35 U.S.C. 154(b) by 233 days.

(21) Appl. No.: 10/516,344

(22) PCT Filed: May 19, 2003

(86) PCT No.: PCT/EP03/05228
§ 371 (c)(1),
(2), (4) Date: Nov. 21, 2005

(87) PCT Pub. No.: WO03/101422
PCT Pub. Date: Dec. 11, 2003

(65) Prior Publication Data
US 2006/0177414 A1   Aug. 10, 2006

(30) Foreign Application Priority Data
May 31, 2002   (DE) .................................. 102 24 086

(51) Int. Cl.
*A61K 31/785*   (2006.01)
(52) U.S. Cl.
USPC ....................................................... 424/78.12

(58) Field of Classification Search
None
See application file for complete search history.

(56) References Cited

U.S. PATENT DOCUMENTS

| | | | |
|---|---|---|---|
| 4,996,222 A | 2/1991 | Carlin et al. | |
| 5,152,986 A * | 10/1992 | Lange et al. | 424/78.14 |
| 5,338,732 A | 8/1994 | Atzinger et al. | |
| 5,385,748 A | 1/1995 | Bunger et al. | |
| 6,323,213 B1 * | 11/2001 | Bartel et al. | 514/300 |
| 6,667,058 B1 * | 12/2003 | Goede et al. | 424/473 |
| 6,995,170 B1 | 2/2006 | Himmler et al. | |
| 2003/0004155 A1 | 1/2003 | Sigg et al. | |
| 2004/0013695 A1 | 1/2004 | Vande-Velde | |

FOREIGN PATENT DOCUMENTS

| | | |
|---|---|---|
| EP | 0 295 495 A1 | 12/1988 |
| EP | 0 564 154 A1 | 10/1993 |
| EP | 0 911 039 A2 | 4/1997 |
| JP | 60204713 | 10/1985 |
| WO | WO 01/05431 A1 | 1/2001 |
| WO | WO 03/007995 A2 | 1/2003 |

OTHER PUBLICATIONS 93106-60-6 CAS Registry Printout.*
195532-12-8 CAS Registry Printout.*
Sriwongjanya, et al., Effect of Ion Exchange Resins on the Drug Release from Matrix Tablets, European Journal of Pharmaceutics and Biopharmaceutics, 1998, 321-327, 46.

* cited by examiner

*Primary Examiner* — Paul Dickinson

(57) ABSTRACT

The present invention relates to pharmaceutical preparations for oral administration, comprising one or more active substances bound to an ion exchanger. In order to improve physical stability and acceptance, particularly in animals, a pseudoplastic gel-former thickener is included.

10 Claims, No Drawings

PHARMACEUTICAL PREPARATIONS FOR ORAL ADMINISTRATION, CONTAINING ION-EXCHANGE RESINS LOADED WITH ACTIVE INGREDIENTS AND INTRINSICALLY VISCOUS GELLING AGENTS AS THICKENING AGENTS

The present invention relates to pharmaceutical preparations for oral administration, comprising one or more active substances bound to an ion exchanger. In order to improve physical stability and acceptance, particularly in animals, a pseudoplastic gel-former thickener is included.

It has long been known to bind active pharmaceutical substances to ion exchange resins in order to make it easier to administer, for example, active substances with a pronounced inherent odor (CH 383 552). It is also known to bind active pharmaceutical substances to ion exchange resins in order to effect uniform release of the active substance over a prolonged period (DE 30 28 082). It is additionally known to bind active anthelmintic substances to ion exchange resins in order to influence the taste of the active substances (DE 30 28 082). By binding to ion exchange resins it is also possible to mask the bitter taste of quinolone antibiotics, so permitting administration to animals (EP-A-295 495).

The abovementioned text describes formulations of bitter-tasting quinolone-carboxylic acid derivatives which are bound to ion exchange resins, and their production. The ion exchange resins in question include weakly acidic cationic types, whose matrix may be gel-like or macroporous. Suitable base monomers for the ion exchangers are polymerizable monomers which by means of appropriate side chains may be functionalized to give cation exchange resins. The ion exchangers are known under the trade names Lewatit®, Amberlite®, Purolite® or Dowex®. Corresponding formulations have been described in veterinary medicine as feed medicaments for pigs.

The often unfavorable surface texture of ion exchangers frequently leads to severe caking of the sediment following settling of the particles in liquid suspensions.

Our patent application WO 03/007995 describes the stabilization of such ion exchangers by grinding so that at least 90% of the particles are smaller than 50 μm. Probably as a result of rounding-off of the irregular surface, the sediments formed are then easily reagitated. Grinding operations of this kind, however, are very laborious and make the production of such preparations significantly more expensive.

It is also known to solidify pharmaceutical preparations by using gel formers (e.g. hydroxyethylcellulose, hydroxypropylcellulose, hydroxymethylpropylcellulose) to such an extent that sedimentation is no longer able to take place. However, semisolid preparations of this kind no longer flow under the force of their own weight. It is difficult to realize liquid pharmaceutical forms with such preparations.

It is known, moreover, that liquid, aqueous suspensions of ion exchange resins can be stabilized using pseudoplastic gel formers (e.g. polyacrylic acid, xanthan, tragacanth, Na carboxymethylcellulose, bentonite). For instance, U.S. Pat. No. 6,146,622 and US 2 002 035 154 describe aqueous suspensions of a cation exchanger which are stabilized with polyacrylic acid (Carbopol 974 P) or xanthan. U.S. Pat. No. 5,612,026 describes a drink mix which comprises an anion exchanger and xanthan. Balkus et al. (Langmuir, 12, 6277-6281 (1996)) publicized the stabilizing of gadolinium-containing hectorite suspensions with xanthan. Further descriptions of aqueous ion exchange suspensions stabilized against sedimentation using pseudoplastic polymers can be found in JP 05 279 245, JP 05 279 246, Sprockel et al., Drug Dev. Ind. Pharm. 15, 1275-1287 (1989), EP 139 881, JP 01 071 823, JP 01 071 822 and JP 63 230 636. In a state of rest suspensions of this kind possess a high viscosity, thereby preventing sedimentation of the suspended ion exchanger particles. Under the effect of force, the system liquefies and so can easily be pumped or sprayed.

Surprisingly it has now been found that suspensions of an ion exchanger with active substance loading that have been thickened with a pseudoplastic polymer have a particularly good mouth feel and are very well accepted and tolerated after oral administration. Such suspensions, moreover, are stable to sedimentation of the solid constituents and have advantageous flow properties desirable in a composition for oral administration. After absorption in the stomach the active pharmaceutical substance is rapidly detached from the ion exchanger. There is therefore little change in the pharmacokinetic profile as compared with unbound active substance.

The invention accordingly provides:
A pharmaceutical preparation comprising one or more active substances bound to an ion exchanger, characterized in that the loaded ion exchanger is dispersed in a carrier medium which comprises at least one pseudoplastic gel former.
The use of pharmaceutical preparations comprising ion exchangers loaded with active substances and at least one pseudoplastic gel former, especially in veterinary medicine.

Examples of pseudoplastic gel formers which can be used include microcrystalline cellulose, cellulose ethers (methylcellulose, hydroxyethylcellulose, hydroxypropylcellulose, methylhydroxypropylcellulose, Na carboxymethylcellulose), xanthan, tragacanth, guar gum, gum arabic, starch and starch derivatives such as Na carboxymethyl starch, gelatin, highly disperse silica (e.g. Aerosil), polyacyrylic acid, aluminium stearate or bentonite. It is also possible to combine the stated gel formers with one another.

Highly disperse silica finds preferred use in the thickening of non-aqueous carrier liquids. For the thickening of aqueous carrier liquids it is preferred to use microcrystalline cellulose, cellulose ethers, xanthan, polyacrylic acid and bentonite or mixtures of the stated gel formers. Particular preference is given in this context to the use of microcrystalline cellulose, Na carboxymethylcellulose, xanthan, polyacrylic acid and bentonite.

The ion exchange resins may have, for example, a gel-like or macroporous matrix. Suitable base monomers for the ion exchangers include polymerizable monomers which by means of appropriate functionalization can be converted into ion exchange resins. Examples of suitable monomers include (meth)acrylates, (meth)acrylonitrile and styrene derivatives. Further comonomers used to prepare the base polymers include polyvinyl compounds such as divinylbenzene, ethylene glycol dimethacrylate or methylenebisacrylamide, for example. Condensation resins which lead to ion exchangers are also suitable, examples being phenol-formaldehyde resins with appropriate functional groups.

The ion exchangers which can be used are known. Further details of various ion exchanger types and their preparation can be found, for example, in Ullmann's Encyclopedia of Industrial Chemistry (Release 2001, 6th Edition). The preferred macroporous resins may have different pore volumes. The degree of crosslinking of the suitable ion exchange resins should preferably be up to 20% and with particular preference up to 12%. The synthetic resins usually have particle sizes of from 1 to 300 μm, preferably from 10 to 200 μm. Examples of customary commercial ion exchange resins are Lewatit®, Amberlite®, Dowex® and Purolite®.

To bind basic or cationic active substances it is possible to use acidic ion exchangers.

Strongly acidic ion exchangers used are preferably those based on poly(styrene, divinylbenzene)sulphonic acid. Examples that may be mentioned include:

Amberlite IRP 69: poly(styrene, divinyibenzene)sulphonic acid in Na form; usual particle size: 10-25%>75 μm, max. 1%>150 μm, K exchange capacity: 110-135 mg/g corresponding to 2.75-3.38 eq/kg Purolite C 100 H MR: poly(styrene, divinylbenzene)sulphonic acid in H form; usual particle size: max. 1%>150 μm, exchange capacity: at least 3.2 eq/kg Purolite C 100 MR: poly(styrene, divinylbenzene)sulphonic acid in Na form, corresponds to Amberlite IRP 69

Lewatit Catalyst K 1481: poly(styrene, divinylbenzene) sulphonic acid in H form; usual particle size: min. 97%<30 μm, exchange capacity: 5.0 eq/kg Lewasorb SW 12: poly(styrene, divinylbenzene)sulphonic acid in Na form, corresponds otherwise to Lewatit K 1481.

As weakly acidic cation exchangers, use is made especially of those based on methacrylic acid-divinylbenzene copolymers. Examples include:

Amberlite IRP 64: methacrylic acid-divinylbenzene copolymer in H form; usual particle size: 15-30%>75 μm, max. 1%>150 μm, exchange capacity: min. 10 eq/kg Purolite C 115 K MR: methacrylic acid-divinylbenzene copolymer in potassium form; usual particle size: max. 1%>150 μm Purolite C 115 H MR: methacrylic acid-divinylbenzene copolymer in H form, otherwise like Purolite C 115 K MR.

Lewatit CNP 105: macroporous methacrylic acid-divinylbenzene copolymer in H form, exchange capacity min. 1.4 eq/l.

To bind acidic and anionic active substances it is possible to use anion exchangers.

Anion exchangers used are preferably polystyrene resins having amine and/or ammonium side groups. Examples that may be mentioned include the following:

Purolite A 430 M R: poly(styrene-divinylbenzene)trimethylammonium chloride, exchange capacity 3.7-4.8 eq/kg Lewatit MP 500:. poly(styrene-divinylbenzene)trimethylammonium chloride, exchange capacity min. 1.1 eq/l Lewatit MP 62 WS: poly(styrene-divinylbenzene)dimethylamine, exchange capacity min. 1.7 eq/l Duolite AP143/1093: poly(styrene-divinylbenzene)trimethylammonium chloride, exchange capacity 3.7-4.8 eq/kg Active pharmaceutical substances having a basic function which are capable of binding to cation exchangers can be used. This is appropriate in particular in the case of medicaments with an unpleasant odour or which lead to an unpleasant taste sensation when administered orally. Examples that may be mentioned of active substances of this kind include quinolone antibiotics and related antibiotics, as disclosed inter alia in the following documents: U.S. Pat. No. 4,670,444 (Bayer AG), U.S. Pat. No. 4,472,405 (Riker Labs), U.S. Pat. No. 4,730,000 (Abbott), U.S. Pat. No. 4,861,779 (Pfizer), U.S. Pat. No. 4,382,892 (Daiichi), U.S. Pat. No. 4,704,459 (Toyama); specific examples include the following: benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, pipemidic acid, temafloxacin, tosufloxacin, sarafloxacin, sparfloxacin.

One preferred group of fluoroquinolones are those of the formula (I) or (II):

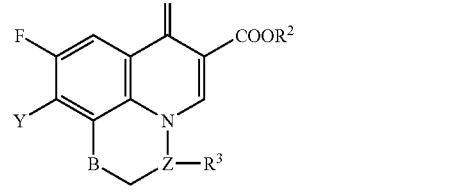

in which

X stands for hydrogen, halogen, $C_{1-4}$-alkyl, $C_{1-4}$-alkoxy, $NH_2$,

Y stands for radicals of the structures

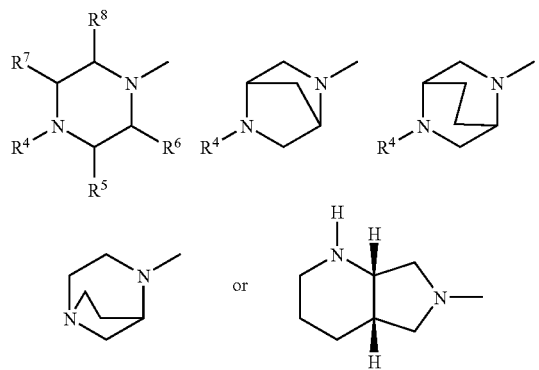

in which $R^4$ stands for optionally hydroxy- or methoxy-substituted straight-chain or branched $C_1$-$C_4$-alkyl, cyclopropyl, acyl having 1 to 3 carbon atoms, $R^5$ stands for hydrogen, methyl, phenyl, thienyl or pyridyl, $R^6$ stands for hydrogen or $C_{1-4}$-alkyl, $R^7$ stands for hydrogen or $C_{1-4}$-alkyl, $R^8$ stands for hydrogen or $C_{1-4}$-alkyl, and also $R^1$ stands for an alkyl radical having 1 to 3 carbon atoms, cyclopropyl, 2-fluoroethyl, methoxy, 4-fluorophenyl. 2,4-difluorophenyl or methylamino, $R^2$ stands for hydrogen or optionally methoxy- or 2-methoxyethoxy-substituted alkyl having 1 to 6 carbon atoms and also cyclohexyl, benzyl, 2-oxopropyl, phenacyl, ethoxycarbonylmethyl, pivaloyloxymethyl, $R^3$ stands for hydrogen, methyl or ethyl and A stands for nitrogen, =CH—, =C(halogen)-, =C(OCH_3)—, =C(CH_3)— or =C(CN), B stands for oxygen, optionally methyl- or phenyl-substituted =NH or =CH_2, Z stands for =CH— or =N—, and their pharmaceutically usable salts and hydrates.

The compounds of the formulae (I) and (II) may also be present in the form of their racemates or in enantiomeric forms.

Preferred compounds of the formula (I) are those in which

A stands for =CH— or =C—CN,
$R^1$ stands for optionally halogen-substituted $C_1$-$C_3$-alkyl or cyclopropyl,
$R^2$ stands for hydrogen or $C_{1-4}$-alkyl,
Y stands for radicals of the structures

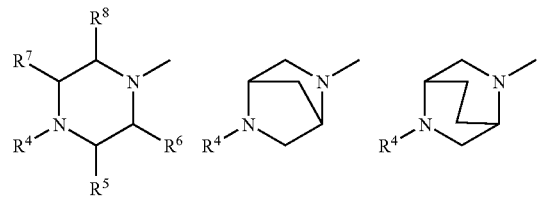

in which
$R^4$ stands for optionally hydroxy-substituted straight-chain or branched $C_1$-$C_3$-alkyl, oxalkyl having 1 to 4 carbon atoms,
$R^5$ strands for hydrogen, methyl or phenyl,
$R^6$, $R^7$, $R^8$ independently of one another stand for hydrogen or methyl,
and their pharmaceutically usable hydrates and salts.

Particularly preferred compounds are those of the formula (I)
in which
A stands for =CH— or =C—CN,
$R^1$ stands for cyclopropyl,
$R^2$ stands for hydrogen, methyl or ethyl,
Y stands for radicals of the structures

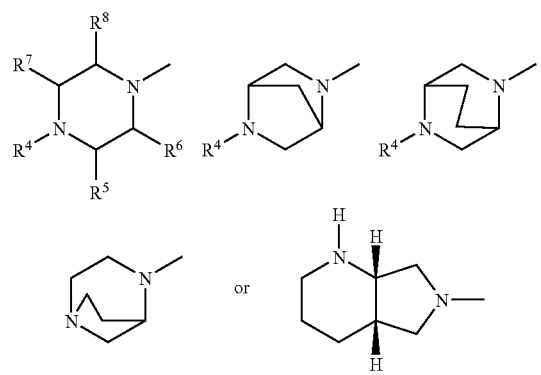

in which
$R^4$ stands for methyl, optionally hydroxy-substituted ethyl,
$R^5$ stands for hydrogen or methyl,
$R^6$, $R^7$, $R^8$ independently of one another stand for hydrogen or methyl,
and their pharmaceutically usable salts and hydrates.

Suitable salts include basic salts and acid addition salts which can be used pharmaceutically.

By salts which can be used pharmaceutically are meant for example the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. The compounds of the invention can also be bound to acidic or basic ion exchangers. As basic salts which can be used pharmaceutically mention may be made of the alkali metal salts, for example the sodium or potassium salts, the alkaline earth metal salts, for example the magnesium or calcium salts; the zinc salts, the silver salts and the guanidinium salts.

By hydrates are meant both the hydrates of the fluoroquinolones themselves and the hydrates of their salts.

Particularly preferred fluoroquinolones include the compounds described in WO 97/31001, especially 8-cyano-1-cyclopropyl-7-((1S,6S)-2,8-diazabicyclo-[4.3.0]nonan-8-yl)-6-fluoro-1,4-dihydro-4-oxo-3-quinolinecarboxylic acid (prado-floxacin) of the formula

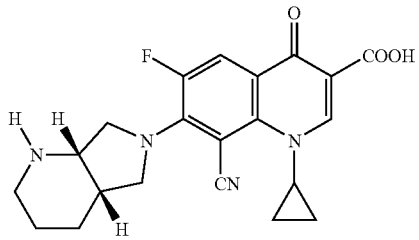 [SMILES: N#Cc1c(N2C[C@@H]3CCCN[C@@H]3C2)c(F)cc2c(=O)c(C(=O)O)cn(C3CC3)c12]

Furthermore, enrofloxacin:
1-cyclopropyl-7-(4-ethyl-1-piperazinyl)-6-fluoro-1, 4-dihydro-4-oxo-3-quinolone-carboxylic acid

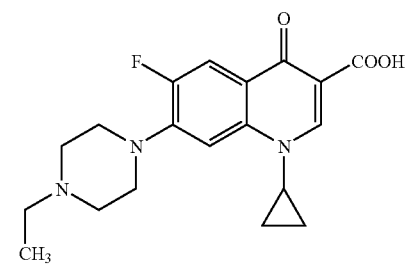 [SMILES: CCN1CCN(c2cc3c(cc2F)c(=O)c(C(=O)O)cn3C2CC2)CC1]

is used with particular preference.

Also suitable, furthermore, are other active substances having a suitable basic function, as specified inter alia in the following documents: U.S. Pat. Nos. 3,536,713, 3,714,159, 3,682,930, 3,177,252; specific examples include the following active substances: ampicillin, amoxicillin, cephazolin, cefotiam, ceftizoxime, cefotaxim, cefodizim, ceftriaxon, ceflazidim, cefsulodin, cefalexin, cefaclor, cefadroxil, cefpodoximproxetil, cefetametpivoxil, cefixim, ceftibuten, loracarbef, imipenem, aztreonam, streptomycin, neomycin, kanamycin, spectinomycin, tetracycline, oxytetracycline, doxycycline, minocycline, erythromycin, clarithromycin, roxithromycin, azithromycin, spiramycin, sulfadiazin, sulfamethoxazole, sulfalene, sulfadoxin, trimethoprim, tetroxoprim, metronidazole, nimorazole, tinidazole, lincomycin, clindamycin, vancomycin, teicoplanin, isoniazid, pyrazinamide, ethambutol, rifampicin, clotrimazole, econazole, isoconazole, oxiconazole, bifonazole, tioconazole, fenticonazole, miconazole, ketoconazole, itraconazole, fluconazole, terbinafin, naftifine, amorolfine, flucytosin, amphotericin B, nystatin, chloroquine, mefloquine, quinine, primraquine, halofantrin, proguanil, pyrimetbamine, melarsoprol, nifurtimox, pentamidine, amantadine, tromantadine, aciclovir, ganciclovir, vidarabine, didanosine, zalcitabin, pyrantel, mebendazole, albendazole, tiabendazole, diethylcarbamazine, pyrvinium, oxamniquine, ambroxol, loperamide, ketotifen, metoclopramide, flupirtine.

It is also possible to bind acid and anionic active substances to anion exchangers. Specific examples that may be mentioned include the following:

acamprosate, aceclofenac, acemetacin, acetylcysteine, acetylsalicylic acid, acitretin, adapalene, alendronic acid, alprostadil, amidotrizoic acid, 4-aminosalicylic acid, amoxicillin, ampicillin, ascorbic acid, atorvastatin, aztreonam, baclofen, benazepril, benzylpenicillin, bezafibrate, biotin, bumetanide, candesartan, potassium canrenoate, captopril, carbidopa, carbocisteine, cefaclor, cefadroxil, cefalexin, cefamandole, cefazolin, cefetamet, cefixim, cefotaxim, cefotiam, cefoxitin, cefpodoxime, ceftibutene, ceftriaxone, cefuroxime, cerivastatin, cetirizine, chenodeoxycholic acid, chlorambucil, cidofovir, cilastatin, cilazapril, clavulanic acid, clodronic acid, dalteparin Na, diclofenac, dicloxacillin, dipotassium clorazepat, dinoprost, enalapril, eprosartan, etacrynic acid, etidronic acid, felbinac, fexofenadin, flucloxacillin, flufenamic acid, flurbiprofen, fluvastatin, folic acid, fosfestrol, fosfomycin, fumaric acid, furosemid, gabapentin, gemfibrozil, heparin, hyaluronic acid, hydrocortisone hydrogensuccinate, ibandronic acid, ibuprofen, iloprost, imidapril, imipenem, indometacin, iotalaminic acid, iotroxic acid, ioxaglic acid, ketoprofen, levocabastine, levodopa, levothyroxin Na, lipoic acid, lisinopril, lodoxamide, lonazolac, loracarbef, mefenamic acid, meropenem, mesalazine, mesna, metamizole, methotrexate, mezlocillin, moexipril, montelukast, moxifloxacin, naproxen, natamycin, nateglinide, Na dibunate, Na iopodate, Na picosulfate, nicotinic acid, olsalazine, orotic acid, oxacillin, pamidronic acid, pangamic acid, penicillamine, perindopril, phenobarbital, phenoxymethylpenicillin, piperacillin, piretanide, pravastatin, probenecid, proglumide, propicillin, quinapril, repaglinide, reviparin Na, risedronic acid, salicylic acid, spirapril, sulfasalazine, tazobactam, telmisartan, tiagabin, tiaprofenic acid, tiludronic acid, tinzaparin Na, trandolapril, tranexamic acid, tretinoin, tryptophan, ursodeoxycholic acid, valproic acid, vigabatrin, zanamivir and zoledronic acid. Mention may also be made of the abovementioned quinolinecarboxylic acids and also structurally related antibiotics.

The analgesic flupirtin mentioned above has the following structural formula:

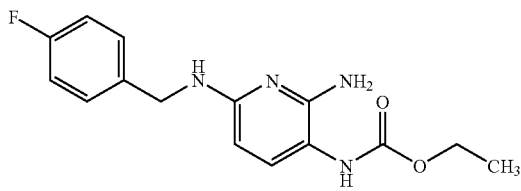 [SMILES: CCOC(=O)Nc1ccc(NCc2ccc(F)cc2)nc1N]

Flupirtin can also be used in the form of its pharmaceutically usable salts, preferably salts with acids, for example the hydrochloride or the maleate.

The ion exchange resins are loaded with active substance in water or polar organic solvents, such as alcohols, for example, such as propylene glycol or ethanol, glycerol, ketones, such as acetone, or mixtures thereof. Water and also alcohol/water mixtures are particularly preferred. Ion exchanger and active substance are stirred in the medium at room temperature or elevated temperature until the active substance is fully bound. The loading of the ion exchanger with active substance and the formulation of the pharmaceutical can also take place in one step.

Where the ion exchanger laden with active substance is to be dispersed in a lipophilic carrier medium which is immiscible with water and/or polar solvent it must first be separated from the aqueous loading medium and dried. Subsequently the loaded ion exchanger can be incorporated into the carrier medium. As a lipophilic carrier medium it is possible for example to use fatty oils, paraffin oils or silicone oils. Preference here is given to the use of fatty oils, examples being medium-chain triglycerides, sesame oil, groundnut oil or soya oil.

The pharmaceutical preparations of the invention are suitable in general for administration in both humans and animals. They are preferably employed in animal keeping and animal breeding in connection with livestock, breeding stock, zoo animals, laboratory animals, experimental animals and pets.

The livestock and breeding stock include mammals such as, for example, cattle, horses, sheep, pigs, goats, camels, water buffalo, donkeys, rabbits, fallow deer, reindeer, furbearing animals such as, for example, mink, chinchilla, racoon, and birds such as, for example, chickens, geese, turkeys, ducks, pigeons and bird species kept in homes and in zoos.

Laboratory and experimental animals include mice, rats, guinea pigs, golden hamsters, dogs and cats.

Pets include rabbits, hamsters, guinea pigs, mice, horses, reptiles, appropriate bird species, dogs and cats.

Fish may also be mentioned, including farmed fish, breeding fish, aquarium fish and ornamental fish of all age levels which live in fresh water and salt water. The farmed fish and breeding fish include, for example, carp, eel, trout, whitefish, salmon, bream, roach, rudd, chub, sole, plaice, halibut, Japanese yellowtail (*Seriola quinqueradiata*), Japanese eel (*Anguilla japonica*), red seabream (*Pagurus major*), seabass (*Dicentrarchus labrax*), grey mullet (*Mugilus cephalus*), pompano, gilthead seabream (*Sparus auratus*), *Tilapia* spp., cichlid species such as, for example, plagioscion, channel catfish. The compositions of the invention are suitable for treating fish fry, e.g. carp of 2 to 4 cm in body length, and in eel feeding.

The preparations of the invention are used preferably in connection with pets such as hamsters, rabbits, guinea pigs, cats and dogs. They are particularly suitable for administration to cats.

Administration may be carried out either prophylactically or therapeutically.

The preparations of the invention are preferably administered orally.

Medicament preparations suitable for animals are those, for example, where a part is played by the improvement of taste during consumption or where the aim is for retarded release of active substance following administration.

To prepare suspensions, the resins loaded with active substance are dispersed very homogeneously in a liquid carrier medium, where appropriate with the assistance of other auxiliaries such as wetting agents. The suspensions are thickened using pseudoplastic gel formers. Further auxiliaries such as wetting agents, antioxidants, preservatives, colorants, and flavourings or aromas may likewise be included.

The preparations of the invention contain the ion exchangers with active substance loading normally in an amount of from 1 to 50% by weight, preferably from 5 to 30% by weight, particularly from 5 to 25% by weight, based on the total weight of the preparation.

Carrier liquids that may be mentioned include water, mixtures of water and water-miscible organic solvents (e.g. alcohols such as ethanol, isopropanol, propylene glycol, glycerol, polyethylene glycol) and also lipophilic carrier liquids (e.g. fatty oils, paraffin oils or silicone oils). In the preparations of the invention the carrier liquid is present in an amount appropriate for the desired consistency, usually from 10 to 98% by weight, preferably from 20 to 90% by weight, based on the total weight of the preparation.

Wetting agents (dispersants) include:
anionic surfactants including emulsifiers such as Na lauryl sulphate, fatty alcohol ether sulphates, mono/dialkyl polyglycol ether orthophosphoric ester monoethanolamine salt, ligninsulphonates or dioctyl sulphosuccinate
cationic surfactants, including emulsifiers such as cetyltrimethylammonium chloride
ampholytic surfactants, including emulsifiers such as di-Na N-lauryl-B-iminodipropionate or lecithin
nonionic surfactants, including emulsifiers, such as p olyoxyethylated castor oil, polyoxyethylated sorbitan fatty acid esters, sorbitan fatty acid esters, glycerol mono- and diglycerides, polyoxyethylene fatty acid esters, polyoxyethylene fatty alcohol ethers; alkylphenol polyglycol ethers, polyethylene-polypropylene block copolymers.

In the preparations of the invention the wetting agent is normally included in an amount of from 0.01 to 10% by weight, preferably from 0.1 to 2% by weight, based on the total weight of the preparation.

Examples of further auxiliaries include:
Preservatives, such as p-hydroxybenzoates, sorbic acid, benzoic acid, propionic acid, formic acid or the salts thereof. In the preparations of the invention the preservative is normally included in an amount of from 0.05 to 2% by weight, preferably from 0.1 to 1% by weight, based on the total weight of the preparation.
Colorants, i.e. all colorants which are approved for use in humans or animals and which may be in dissolved or suspended form. In the preparations of the invention colorants are normally included in an amount of from 0.001 to 5% by weight, preferably from 0.01 to 2% by weight, based on the total weight of the preparation.
Antioxidants such as sulphite or metabisulphites, for example, such as potassium metabisulphite, ascorbic acid, butylated hydroxytoluene, butylated hydroxyanisol, tocopherols. In the preparations of the invention antioxidants are normally present in an amount of from 0.001 to 5% by weight, preferably from 0.01 to 2% by weight, based on the total weight of the preparation.
Flavourings or aromas are those commonly employed in pharmaceuticals, an example being vanillin. In the preparations of the invention flavourings or aromas are normally included in an amount of from 0.001 to 5% by weight, preferably from 0.01 to 2% by weight, based on the total weight of the preparation.

The preparations of the invention can be semisolid (e.g. pastes) or liquid suspensions. The yield point as determinable using a rotational viscometer (e.g. Haake Rheometer RS 100) lies between 0 and 2 000 Pa. The viscosity at $300\ s^{-1}$ amounts to between 10 and 5 000 mPa*s.

The preparations of the invention are preferably liquid suspensions. The yield point lies between 0 and 100 Pa, preferably between 5 and 50 Pa. The viscosity at $300\ s^{-1}$ amounts to between 10 and 1000 mPa*s, preferably between 50 and 500 mPa*s.

The preparation of the invention can be administered separately or together with the feed.

The feed includes feed ingredients of plant origin such as hay, beets, cereals, cereal by-products, feed ingredients of animal origin such as meat, fats, dairy products, bone meal, fish products, and also feed ingredients such as vitamins, proteins, amino acids, for example DL-methionine, salts such as calcium carbonate and sodium chloride. The feed also includes supplementary, formulated and compounded feedstuffs. These contain feed ingredients in a composition which ensures a balanced diet in terms of energy and protein supply and the supply of vitamins, mineral salts and trace elements.

PREPARATION EXAMPLES

Example 1

0.18 kg of methyl p-hydroxybenzoate and 0.02 kg of propyl p-hydroxybenzoate are dissolved in 75.0 kg of hot water. 0.3 kg of xanthan (Xantural 180, CP Kelco) and 0.3 kg of bentonite (Veegum, Vanderbildt) are incorporated into the solution with vigorous stirring, and the mixture is stirred at 70° C. for one hour. After the resultant sol has cooled, 6.0 kg of pradofloxacin, 18.0 kg of a weakly acidic ion exchanger (Amberlite IRP 64) and 1.0 kg of vanillin are dispersed therein. The total batch is then homogenized with a rotor-stator. The result is a viscous suspension.

Example 2

As Example 1, but using 0.2 kg of cream caramel aroma instead of 1.0 kg of vanillin.

Example 3

0.2 kg of sorbic acid and 0.02 kg of ascorbic acid are dissolved in 74.98 kg of hot water. 0.3 kg of xanthan (Xantural 180, CP Kelco) and 0.3 kg of bentonite (Veegum, Vanderbildt) are incorporated into the solution with vigorous stirring, and the mixture is stirred at 70° C. for one hour. After the resultant sol has cooled, 6.0 kg of pradofloxacin, 18.0 kg of a weakly acidic ion exchanger (Amberlite IRP 64) and 0.2 kg of a cream caramel aroma are dispersed therein. The total batch is then homogenized with a rotor-stator. The result is a viscous suspension.

Example 4

As Example 1, but using 0.1 kg of vanilla aroma instead of 1.0 kg of vanillin.

Example 5

0.2 kg of sorbic acid is dissolved in 30.0 kg of propylene glycol. 0.7 kg of xanthan (Xantural 180, CP Kelco) is incorporated into this solution with vigorous stirring. In a second vessel 2.5 kg of pradofloxacin, 0.02 kg of ascorbic acid and 0.2 kg of a vanilla aroma are dissolved in 61.58 kg of water. 10.0 kg of weakly acidic cation exchanger (Amberlite IRP 64) are dispersed in the solution. Using a high-speed stirrer, the xanthan/propylene glycol dispersion is incorporated into this suspension. The total batch is then homogenized with a rotor-stator. The result is a viscous suspension.

Example 6

0.2 kg of sorbic acid is dissolved in 30.0 kg of glycerol. 0.5 kg of xanthan (Xantural 180, CP Kelco) is incorporated into this solution with vigorous stirring. In a second vessel 6.0 kg of pradofloxacin are dissolved in 48.3 kg of water. 10.0 kg of weakly acidic cation exchanger (Amberlite IRP 64) and 5.0 kg of a meat aroma are dispersed in the solution. Using a high-speed stirrer, the xanthan/glycerol dispersion is incorporated into this suspension. The total batch is then homogenized with a rotor-stator. The result is a viscous suspension.

Example 7

5.00 kg of enrofloxacin and 20.00 kg of Purolite C 100 H MR are suspended in 80.00 kg of purified water and the suspension is stirred at room temperature for at least 8 hours. Following sedimentation, the supernatant is drained off. The residue is dried with a filter drier at 75° C. In parallel with this, 0.384 kg of sorbic acid is dissolved in 146.496 kg of hot water. In a second vessel 0.96 kg of polyacrylic acid (Carbopol 974P, BFGoodrich) is dispersed in 19.20 kg of glycerol. 24.00 kg of the dried, laden ion exchanger are suspended therein.

Example 8

5.00 kg of pradofloxacin and 20.00 kg of Purolite C 115 HMR are suspended in 75.00 kg of purified water. Then 0.25 kg of benzoic acid and 0.5 kg of bentonite (Veegum, Vanderbildt) are incorporated with vigorous stirring and the mixture is heated at 70° C. for 1 hour to give a liquid suspension.

Example 9

0.2 kg of sorbic acid are dissolved in 30.0 kg of propylene glycol. 2.25 kg of a mixture of microcrystalline cellulose and Na carboxymethylcellulose (Avicel CL 611, FMC) are incorporated into this solution with vigorous stirring. In a second vessel 6.0 kg of pradofloxacin, 0.02 kg of ascorbic acid and 0.2 kg of a vanilla aroma are dissolved in 54.35 kg of water. 18.0 kg of weakly acidic cationic exchanger (Amberlite IRP 64) are dispersed in the solution. Using a high-speed stirrer, the gel former/propylene glycol dispersion is incorporated into this suspension. The total batch is then homogenized with a rotor-stator. The result is a viscous suspension.

Example 10

6.0 kg of pradofloxacin are stirred together with 18.0kg of Amberlite IRP 64 in 72 kg of water for 16 h. After the suspended particles have settled the supernatant is drained off and the residue is dried at 70° C. This ion exchanger, laden with active substance, is dispersed together with 1.0 kg of vanillin in 72.0 kg of medium-chain triglyericdes (Miglyol 812). Following the addition of 3.0 kg of highly disperse silica (Aerosil 200) the batch is homogenized with a rotor-stator. The result is a viscous suspension.

Example 11

2.50 kg of flupirtine and 7.50 kg of Amberlite IRP 69 are suspended in 40.00 kg of 50% (v/v) ethanol and the suspension is stirred at 40° C. for at least 12 hours. The suspension is transferred to a filter drier, filtered and dried at 60° C. The laden ion exchanger and 0.80 kg of Na carboxymethylcellulose (Blanose 7M31CF, Hercules) are subsequently dispersed in 29.20 kg of purified water with vigorous stirring. The result is a liquid suspension.

Example 12

3.0 kg of flupirtine maleate are stirred together with 12.0 kg of Purolite C115 KMR in 60.0 kg of water for 16 h. Following filtration the residue is dried at 70° C. In a second preparation vessel 0.5 kg of sorbic acid are dissolved in 82.24 kg of medium-chain triglycerides (Miglyol 812). Dispersed therein homogeneously using a rotor-stator are 0.25 kg of caramelaroma, 0.01 kg of red iron oxide and the ion exchanger, laden with active substance. With vigorous stirring 2.0 kg of highly disperse silica (Aerosil 200) are added and the composition is dispersed with a rotor-stator. The result is a liquid suspension.

Example 13

3.0 kg of flupirtine maleate, 12.0 kg of Purolite C115 KMR, 0.25 kg of caramelaroma and 0.01 kg of red iron oxide are dispersed homogeneously in 62.14 kg of water using a rotor-stator. The batch is subsequently stirred for 16 h. In a second vessel 0.1 kg of sorbic acid are dissolved in 20.0 kg of propylene glycol and dispersed therein are 2.5 kg of a mixture of microcrystalline cellulose and Na carboxymethylcellulose (Avicel CL 611). This suspension is added with vigorous stirring to the suspension containing active substance and the composition is homogenized with a rotor-stator. The result is a viscous suspension.

Biological Example

Palatability Test

Owing to their good mouth feel, which can also be attributed to their particular consistency, the pharmaceutical preparations of the invention feature excellent palatability, in cats for example. Table 1 below summarizes the results of a corresponding test on cats:

TABLE 1

Palatability of inventive Examples 1-4, 10 in cats in comparison to a readily palatable reference formulation (nutri-plus Cat, virbac animal medicament, Bad Oldesloe), n = 36.

| | Example | | | | | Reference |
|---|---|---|---|---|---|---|
| | 1 | 2 | 3 | 4 | 10 | |
| Palatability score | 3.5 | 3.4 | 3.5 | 3.4 | 3.3 | 3.5 |
| Salivation following administration | 0% | 0% | 0% | 5.5% | 11.1% | 0% |

Score: 1 = unacceptable, 2 = difficult administration, 3 = moderate consumption, 4 = easy to administer, 5 = very easy to administer Composition of the examples: see above

The invention claimed is:

1. A liquid pharmaceutical preparation comprising pradofloxacin bound to an ion exchange resin dispersed in a carrier medium comprising water and xanthan as a pseudoplastic gel former, wherein the concentration of xanthan in the preparation is from 0.3% to 0.7% by weight.

2. The pharmaceutical preparation according to claim 1, wherein the ion exchange resin is an acidic ion exchanger.

3. The pharmaceutical preparation according to claim 1, wherein the loading of ion exchange resin with pradofloxacin in the preparation is from 1% to 50% by weight, based on the total weight of the preparation.

4. The pharmaceutical preparation according to claim 1, wherein the loading of ion exchange resin with pradofloxacin in the preparation is from 5% to 30% by weight, based on the total weight of the preparation.

5. The pharmaceutical preparation according to claim 1, wherein the carrier medium is from 10 to 98% by weight of the total preparation.

6. The pharmaceutical preparation according to claim 1, wherein the carrier medium is from 20% to 90% by weight of the total preparation.

7. The pharmaceutical preparation according to claim 1, wherein the loading of ion exchange resin with pradofloxacin in the preparation is from 5% to 25% by weight, based on the total weight of the preparation.

8. The pharmaceutical preparation according to claim 1, further comprising bentonite.

9. The pharmaceutical preparation according to claim 1, wherein the concentration of xanthan in the preparation is from 0.5% to 0.7% by weight.

10. The pharmaceutical preparation according to claim 1, wherein the concentration of xanthan in the preparation is about 0.7% by weight.

\* \* \* \* \*

UNITED STATES PATENT AND TRADEMARK OFFICE
CERTIFICATE OF CORRECTION

| | | |
|---|---|---|
| PATENT NO. | : 8,545,829 B2 | Page 1 of 1 |
| APPLICATION NO. | : 10/516344 | |
| DATED | : October 1, 2013 | |
| INVENTOR(S) | : Mertin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 629 days.

Signed and Sealed this
Third Day of March, 2015

Michelle K. Lee
*Deputy Director of the United States Patent and Trademark Office*